United States Patent [19]
Diederich et al.

[11] Patent Number: 5,891,900
[45] Date of Patent: Apr. 6, 1999

[54] OXOPYROLO-PYRROLE DERIVATIVES HAVING THROMBIN INHIBITING ACTIVITY

[75] Inventors: François Diederich; Ulrike Obst, both of Zürich, Switzerland; Lutz Weber, Grenzach-Wyhlen, Germany

[73] Assignee: Hoffman-La Roche Inc, Nutley, N.J.

[21] Appl. No.: 889,862

[22] Filed: Jul. 8, 1997

[30] Foreign Application Priority Data

Jul. 18, 1996 [EP] European Pat. Off. ............. 96111553

[51] Int. Cl.⁶ .................. A61K 31/40; C07D 487/02; C07D 487/04
[52] U.S. Cl. ................. 514/411; 548/428; 548/453
[58] Field of Search ................ 548/428; 514/411

[56] References Cited

U.S. PATENT DOCUMENTS 5,686,459 11/1997 Diederich et al. .................. 514/260

FOREIGN PATENT DOCUMENTS

728758 A1 8/1996 European Pat. Off. .

OTHER PUBLICATIONS

M. Dixon, "The Determination of Enzyme Inhibitor Constants" J. Biochem, 55:170–171 (1953).

Primary Examiner—Alan L. Rotman
Attorney, Agent, or Firm—George W. Johnston; William H. Epstein; John P. Parise

[57] ABSTRACT

Compounds of the formula

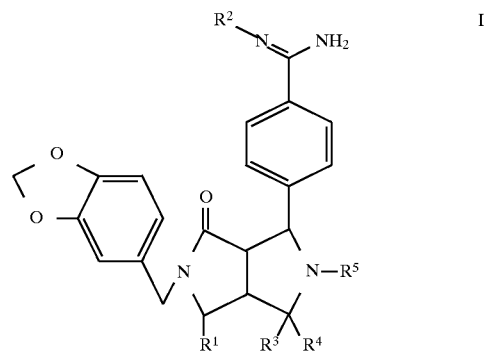

wherein
  $R^1$ is lower-alkyl, cycloalkyl or phenyl,
  $R^2$ is H, OH or C(O)O—A, wherein A is lower-alkyl, cycloalkyl or phenyl, and
  $R^3, R^4$ and $R^5$ are either methyl or $R^3$ is H and $R^4$ and $R^5$ taken together are trimethylene as well as hydrates or solvates and physiologically usable salts thereof can be used for the production of medicaments for the treatment or prophylaxis of illnesses which are caused by thrombin-induced platelet aggregation or fibrinogen clotting in blood plasma.

28 Claims, No Drawings

OXOPYROLO-PYRROLE DERIVATIVES HAVING THROMBIN INHIBITING ACTIVITY

SUMMARY OF THE INVENTION

The invention is concerned with novel oxopyrolo-pyrrole derivatives, especially those of the formula:

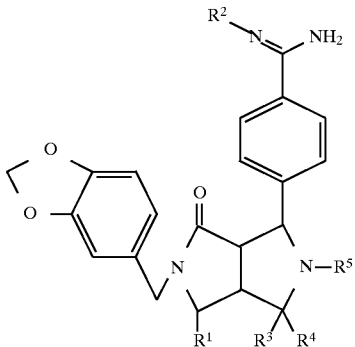

wherein
$R^1$ is lower-alkyl, cycloalkyl or phenyl,
$R^2$ is H, OH or C(O)O—A, wherein A is lower-alkyl, cycloalkyl or phenyl, and
$R^3$, $R^4$ and $R^5$ are either methyl or $R^3$ is H and $R^4$ and $R^5$ taken together are trimethylene as well as hydrates or solvates and physiologically usable salts thereof.

Further, the invention is concerned with a process for the manufacture of the above compounds, pharmaceutical preparations which contain such compounds as well as the use of these compounds in the production of pharmaceutical preparations.

DETAILED DESCRIPTION OF THE INVENTION

Physiologically usable salts of the compounds of the invention are salts with physiologically compatible mineral acids such as hydrochloric acid, sulphuric acid, sulphurous acid or phosphoric acid; or with organic acids such as methanesulphonic acid, p-toluenesulphonic acid, acetic acid, trifluoroacetic acid, citric acid, fumaric acid, maleic acid, tartaric acid, succinic acid or salicylic acid. The compounds of the invention which have acidic groups such as the carboxyl group can also form salts with physiologically compatible bases. Examples of such salts are alkali metal, alkaline earth metal, ammonium and alkylammonium salts such as the Na, K, Ca or tetramethylammonium salt. The compounds of the invention can also be present in the form of zwitterions.

The compounds of the invention can be solvated, especially hydrated. The hydration can be effected in the course of the manufacturing process or can occur gradually as a consequence of hygroscopic properties of an initially anhydrous compound of formula I.

The compounds of the invention contain at least four asymmetric C atoms and can therefore be present as a diastereomer mixture, as an enantiomer mixture or as an optically pure compound.

In the scope of the present invention "lower" denotes a straight-chain or branched group containing up to 6 C atoms. Preferred lower-alkyl groups contain up to 4 C atoms. Examples thereof are methyl, isopropyl, butyl, isobutyl, sec-butyl and tert.butyl. Cycloalkyl encompasses rings containing from 3 to 6 C atoms.

The preferred groups $R^1$ are methyl, ethyl, isopropyl, cyclopropyl, cyclohexyl and phenyl. The preferred groups $R^2$ are hydrogen, hydroxy and COOCH$_3$.

Preferred compounds of the invention are those in which $R^1$ is lower-alkyl, $R^2$ is H and $R^3$, $R^4$ and $R^5$ are methyl, particularly (1RS,3aSR,4SR,6aSR)-4-(5-benzo[1,3]dioxol-5-ylmethyl-4-isopropyl-2,3,3-trimethyl-6-oxo-octahydro-pyrrolo[3,4-c]pyrrol-1-yl)-benzimidamide.

Also preferred are compounds of the invention in which $R^3$ is H and $R^4$ and $R^5$ together are trimethylene and $R^1$ and $R^2$ are as in formula I, especially in which $R^1$ is lower-alkyl or cycloalkyl and $R^2$ is H, particularly
(1RS,3aSR,4RS,6aRS)-4-(2-benzo[1,3]dioxol-5-ylmethyl-1-isopropyl-3-oxo-decahydro-pyrrolo[3,4-a]pyrrolizin-4-yl)-benzimidamide,
(1RS,3aSR,4RS,6aRS)-4-(2-benzo[1,3]dioxol-5-ylmethyl-1-cyclopropyl-3-oxo-decahydro-pyrrolo[3,4-a]pyrrolizin-4-yl)-benzimidamide and
(1RS,3aSR,4RS,6aRS)-4-(2-benzo[1,3]dioxol-5-ylmethyl-1-ethyl-3-oxo-decahydro-pyrrolo[3,4-a]pyrrolizin-4-yl)-benzimidamide.

Further compounds of the invention in which $R^3$, $R^4$ and $R^5$ are methyl are
(1RS,3aSR,4SR,6aSR)-4-(5-benzo[1,3]dioxol-5-ylmethyl-2,3,3,4-tetramethyl-6-oxo-octahydro-pyrrolo[3,4-c]pyrrol-1-yl)-benzimidamide,
(1RS,3aSR,4SR,6aSR)-4-(5-benzo[1,3]dioxol-5-ylmethyl-4-ethyl-2,3,3-trimethyl-6-oxo-octahydro-pyrrolo[3,4-c]pyrrol-1-yl)-benzimidamide,
(1RS,3aSR,4RS,6aRS)-4-(5-benzo[1,3]dioxol-5-ylmethyl-4-cyclohexyl-2,3,3-trimethyl-6-oxo-octahydro-pyrrolo[3,4-c]pyrrol-30 1-yl)-benzimidamide and
(1RS,3aSR,4RS,6aRS)-4-(5-benzo[1,3]dioxol-5-ylmethyl-4-isopropyl-2,3,3-trimethyl-6-oxo-octahydro-pyrrolo[3,4-c]pyrrol-1-yl)-N-hydroxy-benzimidamide.

Further examples of compounds of the invention in which $R^3$ is H and $R^4$ and $R^5$ together are trimethylene, i.e., of the formula:

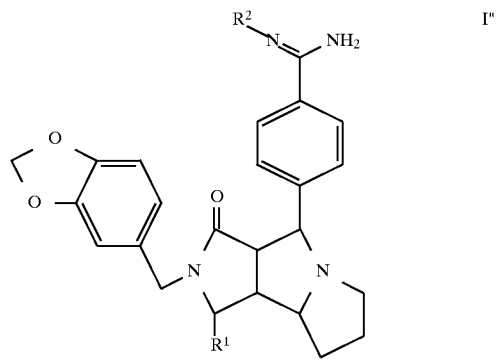

are
(1RS,3aSR,4RS,6aRS)-4-(2-benzo[1,3]dioxol-5-ylmethyl-1-cyclohexyl-3-oxo-decahydro-pyrrolo[3,4-a]pyrrolizin-4-yl)-benzimidamide and
(1RS,3aSR,4RS,6aRS)-4-(2-benzo[1,3]dioxol-5-ylmethyl-3-oxo-1-phenyl-decahydro-pyrrolo[3,4-a]pyrrolizin-4-yl)- benzimidamide.

The compounds of the invention can be manufactured in a manner known per se, e.g., by converting the cyano group (CN) in a corresponding nitrile of formula 11 hereinafter into an amidino group C(N-R$^2$)NH$_2$.

In order to convert CN into C(NH)NH$_2$, the nitrile starting material in a solvent such as ethanol or methanol or a solvent mixture such as chloroform and methanol or chloroform and ethanol can be gassed with a dry stream of hydrogen chloride, preferably at a temperature below 10° C. The reaction solution is treated with a solvent such as diethyl ether and the intermediate which is thus precipitated is filtered off. Thererafter, the intermediate can be dissolved in water, neutralized with a base such as sodium carbonate or sodium hydroxide and the aqueous phase can be extracted with a solvent such as dichloromethane, chloroform or ethyl acetate. The thus-obtained material is treated in a solvent such as methanol or ethanol either with gaseous ammonia or an ammonium salt such as ammonium chloride, preferably at a temperature up to 80° C. Alternatively, the filtered-off intermediate can be directly treated with gaseous ammonia or an ammonium salt in methanol or ethanol.

In order to convert CN into $C(NOH)NH_2$, the nitrile starting material is dissolved in a solvent such as DMF and added to a solution of an inorganic base such as sodium hydride or sodium hydroxide and hydroxylamine or a salt of hydroxylamine with an inorganic acid, such as hydroxylamine hydrochloride, conveniently at a temperature below 0° C.

By reacting a compound of formula I in which $R^2$ is H in a solvent such as dichloromethane or DMF with a chloroformic acid ester of the formula $ClC(O)O$—A there is obtained the corresponding compound in which $R^2$ is the group $C(O)O$—A.

A compound of the formula

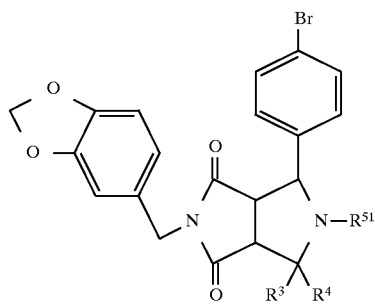

III is obtained by reacting an α-aminocarboxylic acid of the formula $R^{51}$-NHC($R^3$,$R^4$)COOH, wherein $R^{51}$ is H or has the same significance as $R^5$ in formula I, with 4-bromobenzaldehyde and N-piperonyl-maleimide.

This reaction is preferably carried out in a solvent such as DMF, DMSO, acetonitrile, THF, diethyl ether, benzene, toluene, ethyl acetate, methanol or ethanol at a temperature between 0° C. and 160° C. In an especially advantageous embodiment, the reaction is carried out at an elevated temperature in either DMF, DMSO or toluene. It is also advantageous to carry out the reaction at elevated temperature in methanol with the addition of catalytic amounts of acetic acid or in acetonitrile at room temperature with the addition of silver acetate and a tertiary nitrogen base such as triethylamine, diazabicyclooctane or ethylmorpholine.

Where $R^{51}$ is H, the compound III can be N-methylated, e.g., by reaction with an aqueous solution of formic acid and formalin at elevated temperature.

A compound of formula III in which $R^{51}$ has the same significance as $R^5$ in formula I can be reduced, e.g., in THF at about −78° C. with a solution of lithium triethylborohydride in THF, to a compound of the formula:

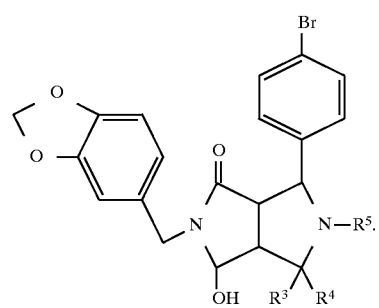

IV

By reacting toluenesulphinic acid with the hydroxypyrrolane IV in $CH_2Cl_2$ in the presence of $CaCl_2$ there is obtained the corresponding toluenesulphonic acid ester. By reacting such an ester with a compound of the formula $R^1$-MgCl there is obtained a compound of the formula:

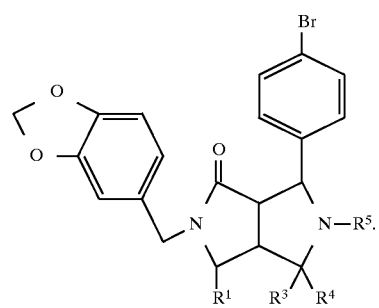

V

This reaction can be carried out, for example, by reacting a solution of $ZnCl_2$ in THF in a solvent such as $CH_2Cl_2$ firstly with a solution of $R^1$-MgCl in THF and then with a solution of the toluenesulphonic acid ester of a hydroxypyrrolone of formula IV in $CH_2Cl_2$.

By heating a bromide V and CuCN in DMF under reflux there is obtained the corresponding nitrile of the formula:

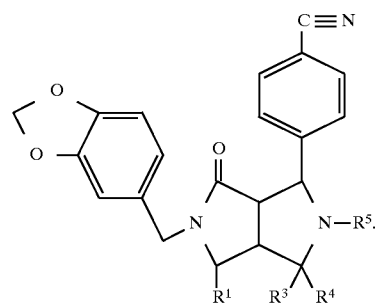

II

Moreover, many of the Examples hereinafter contain detailed information concerning the preparation of certain starting materials and intermediates.

The compounds of the invention, their solvates and their salts inhibit not only thrombin-induced platelet aggregation, but also thrombin-induced clotting of fibrinogen in blood plasma. The said compounds influence not only platelet-induced, but also plasmatic blood clotting. They therefore prevent especially the formation of hyaline thrombi and of platelet-rich thrombi and can be used in the control, treatment or prevention of illnesses which are known to be caused by thrombus formation, such as thrombosis and diseases which result from thrombosis, such as stroke and cardiac infarct. The compounds of the invention are also useful for the control, treatment and prevention of thrombus-induced inflammation and for treating arteriosclerosis. Further, these compounds have an effect on tumour cells and prevent the formation of metastases. Accordingly, they can also be used as antitumour agents.

A differential inhibition of thrombin and other serine proteases by the compounds of the invention is desirable in order to obtain compounds having as high a specificity as possible and at the same time to avoid possible side effects. The ratio of the inhibition of trypsin to the inhibition of thrombin was taken as the general measurement for the specificity of a compound ("q" in the Table hereinafter), because trypsin, as the most non-specific serine protease, can be readily inhibited by the widest variety of inhibitors. In order for the inhibition of thrombin and trypsin to be directly comparable in spite of the use of different substrates, the inhibition constant $K_i$ independent of substate and enzyme concentration was determined as the measurement of the inhibition.

Specific chromogenic peptide substrates can be used to determine the inhibition of the catalytic activity of the above proteases. The inhibition of the amidolytic activity of thombin and trypsin by the above compounds was determined as described hereinafter.

The measurements were carried out on microtitre plates at room temperature. For this, in each well of the plate 150 $\mu$l of buffer (50 mM Tris, 100 mM NaCl, 0.1% polyethylene glycol; pH 7.8) were mixed with 50 $\mu$l of the inhibitor dissolved in DMSO and diluted in the buffer, and 25 $\mu$l of human thrombin (0.5 nM final conc.) were added. After incubation for 10 minutes the reaction was started by the addition of chromogenic substrate S-2238 (H-D-Phe-Pip-Arg-paranitroanilide from Kabivitrum; 10 or 50 $\mu$M final concentration) and the hydrolysis of the substrate was followed spectrophotometrically on a kinetic microtitre plate reader for 5 minutes. After graphical presentation of the inhibition curves the $K_i$ values were determined according to the method described in *Biochem. J.*, 55, 1955, 170–171. The inhibition of trypsin was effected analogously, but using the substrate S-2251 (H-D-Val-Leu-Lys-paranitroaniline) in 200 and 750 $\mu$M final concentration.

The results will be evident from the following Table:

| Product of Example | $K_i$ ($\mu$M) thrombin | $K_i$ ($\mu$M) trypsin | q |
|---|---|---|---|
| 1    | 1.9   | 60   | 31   |
| 2.A) | 0.095 | 7.3  | 76   |
| 2.B) | 0.030 | 6.7  | 222  |
| 2.C) | 0.860 | 33.0 | 38   |
| 2.D) | 0.005 | 7.5  | 1500 |
| 2.E) | 1.7   | 4.4  | 2.5  |
| 2.F) | 1.4   | 5.2  | 3.7  |
| 2.G) | 0.010 | 2.3  | 230  |
| 2.H) | 0.008 | 1.7  | 210  |

As mentioned earlier, pharmaceutical preparations containing, in a pharmaceutically acceptable carrier, a compound of the invention, or a solvate or salt thereof are likewise encompassed by the present invention. Also within the scope of the present invention is a process for the production of such pharmaceutical preparations which comprises bringing one or more of the said compounds and, if desired, other therapeutically valuable substances, into a galenical administration form. These pharmaceutical preparations can be administered orally, e.g., in the form of tablets, dragées, hard and soft gelatine capsules, solutions, emulsions or suspensions, or rectally, e.g., in the form of suppositories, or as a spray. The administration can, however, also be affected parenterally, e.g., in the form of injection solutions.

The invention encompasses pharmaceutical preparations, such as unit dosage forms for oral and rectal adminstration, and solutions, emulsions or suspensions that are not administered in the form of a unit dosage form.

In the unit dosage forms of the invention, the active substance can be mixed with conventional pharmaceutically inert, inorganic or organic excipients (a "carrier") for the production of tablets, coated tablets, dragées and hard or soft gelatine capsules for oral administration. Lactose, corn starch or derivatives thereof, talc, stearic acid or its salts can be used, e.g., as such excipients for tablets, coated tablets, dragees and hard gelatine capsules. Suitable excipients for soft gelatine capsules are, e.g., vegetable oils, waxes, fats, semi-solid and liquid polyols. Depending on the nature of the active substance, no excipients are, however, usually required in the case of soft gelatine capsules.

Suitable excipients for the production of a carrier for solutions and syrups containing a compound of the invention are, e.g., water, polyols, sucrose, invert sugar and glucose. Suitable excipients for the production of a carrier for injection solutions containing a compound of the invention are, e.g., water, alcohols, polyols, glycerol and vegetable oils. Unit dosage forms of the invention may also be in the form of suppositories. Suitable excipients for the production of a carrier for suppositories containing a compound of the invention are natural or hardened oil, waxes, fats, semi-liquid or liquid polyols.

The carriers in the pharmaceutical preparations of the invention can also contain conventional preservatives, solubilizers, stabilizers, wetting agents, emulsifiers, sweeteners, colorants, flavorants, salts for varying the osmotic pressure, buffers, coating agents or antioxidants.

The present invention also comprises a method of inhibiting thrombus formation in a host in need of such inhibition, which method comprises administering to said host a pharmaceutical preparation containing, in a pharaceutically acceptable carrier, a compound of the invention herein described and claimed in an amount sufficient to inhibit said thrombus formation in said host.

It is a known treatment for thrombosis to administer to a host who is suffering from thrombosis a drug which inhibits thrombus formation. The host's own circulatory system then gradually removes the thrombus. Examples of drugs known in the art for such treatment of thrombosis are heparin and wafarin. Therefore, the present invention also comprises a method of treating thrombosis in a host in need of such treatment, which method comprises administering to said host a pharmaceutical preparation containing, in a pharaceutically acceptable carrier, a compound of the invention herein described and claimed in an amount sufficient to treat said thrombosis in said host.

For the inhibition of thrombus formation and for the control, treatment or prevention of thrombosis and the resultant illnesses mentioned above, the dosage of the active substance can vary within wide limits and will, of course, be fitted to the individual requirements in each particular case. Such dosages may be determined by any conventional means, such as through dose-limiting clinical studies. In general, in the case of oral or parenteral, e.g., intravenous or subcutaneous, administration a dosage of about 0.1 to 20 mg/kg, preferably of about 0.5 to 4 mg/kg, per day should be appropriate for adults, although the upper limit just given can also be exceeded or gone below when this is shown to be indicated.

EXAMPLE 1

Dry HCl is conducted at 0° C. for 10 min. into a solution of (1RS,3aSR,4SR,6aSR)-4-(5-benzo[1,3]dioxol-5-ylmethyl-2,3,3,4-tetramethyl-6-oxo-octahydro-pyrrolo[3,4- c]pyrrol-1-yl)-benzonitrile (0.295 g, 0.707 mmol) in dry chloroform (1.8 ml) and dry methanol (0.35 ml). Thereafter, the reaction mixture is left to stand at 4° C. for 24 h. The solid which separates after the addition of diethyl ether is dried under a high vacuum and thereafter dissolved in methanol (2 ml). Methanolic ammonia solution is added until the smell of ammonia remains. The reaction mixture is stirred at 65° C. for 3.5 h. After cooling the NH$_4$Cl is precipitated with acetone and filtered off. The solvent is removed by distillation, the residue is dissolved in ethanol and the product is precipitated slowly with diethyl ether. Yield 0.298 g (90%) of (1RS,3aSR,4SR,6aSR)-4-(5-benzo[1,3]dioxol-5-ylmethyl-2,3,3,4-tetramethyl-6-oxo-octahydro-pyrrolo[3,4-c]pyrrol-1-yl)-benzimidamide hydrochloride. Colourless solid. M.p. from 190° C. dec. DEI-MS: 435.3 ([M+H]$^+$, 8); 434.3 ([M]$^+$, 6); 419.2 ([M-CH$_3$]$^+$; 12) 214.2 (22); 197.1 (12); 135.1 (99); 83.1 (100).

EXAMPLE 2

The following compounds are prepared analogously to Example 1:

2.A) (1RS,3aSR,4SR,6aSR)-4-(5-Benzo[1,3]dioxol-5-ylmethyl-4-ethyl-2,3,3-trimethyl-6-oxo-octahydro-pyrrolo[3,4-c]pyrrol-1-yl)-benzimidamide hydrochloride. Yield 90%. Colourless foam. M.p. from 270° C. dec. DEI-MS: 448.3 ([M]$^+$, 47); 433.3 (100); 214.2 (35); 135.1 (45).

2.B) (1RS,3aSR,4RS,6aSR)-4-(5-Benzo[1,3]dioxol-5-ylmethyl-4-isopropyl-2,3,3-trimethyl-6-oxo-octahydro-pyrrolo[3,4-c]pyrrol-1-yl)-benzimidamide hydrochloride. Yield 66%. Colourless solid. M.p. from 250° C. dec. DEI-MS: 462.3 ([M]$^+$, 33); 447.2 (100); 430.3 (21); 214.2 (30); 135.1 (67).

2.C) (1RS,3aSR,4RS,6aSR)-4-(5-Benzo[1,3]dioxol-5-ylmethyl-4-cyclohexyl-2,3,3-trimethyl-6-oxo-octahydro-pyrrolo[3,4-c]pyrrol-1-yl)-benzimidamide hydrochloride. Yield 74%. Colourless solid. M.p. 195°–199° C. DEI-MS: 502.2 ([M]$^+$, 11); 487.2 (42); 214.1 (38); 135 (100).

2.D) (1RS,3aSR,4RS,6aRS)-4-(2-Benzo[1,3]dioxol-5-ylmethyl-1-isopropyl-3-oxo-decahydro-pyrrolo[3,4-a]pyrrolizin-4-yl)-benzimidamide hydrochloride. Yield 79%. Colourless solid. M.p. 210°–215° C. DEI-MS: 460.2 ([M]$^+$, 33); 201.1 (84); 184.1 (37); 172.1 (23); 135.0 (100).

2.E) (1RS,3aSR,4RS,6aRS)-4-(2-Benzo[1,3]dioxol-5-ylmethyl-1-cyclohexyl-3-oxo-decahydro-pyrrolo[3,4-a]pyrrolizin-4-yl)-benzimidamide hydrochloride. Yield 72%. Colourless solid. M.p. 219°–224° C. DEI-MS: 500.2 ([M]$^+$, 18); 483.1 (6); 349.1 (5); 201.1 (77); 184.1 (75); 135.1 (100).

2.F) (1RS,3aSR,4RS,6aRS)-4-(2-Benzo[1,3]dioxol-5-ylmethyl-3-oxo-1-phenyl-decahydro-pyrrolo[3,4-a]pyrrolizin-4-yl)-benzimidamide hydrochloride. Yield 89%. Colourless solid. M.p. >195° C. dec. DEI-MS: 494.2 ([M]$^+$, 18); 477.2 (14); 342.2 (7); 201.2 (49); 184.1 (100); 135.1 (74).

2.G) (1RS,3aSR,4RS,6aRS)-4-(2-Benzo[1,3]dioxol-5-ylmethyl-1-cyclopropyl-3-oxo-decahydro-pyrrolo[3,4-a]pyrrolizin-4-yl)-benzimidamide hydrochloride. Yield 62%. Colourless solid. M.p. >165° C. dec. DEI-MS: 458.2 ([M]$^+$, 23); 441.2 (10); 201.2 (54); 184.1 (75); 135.1 (100).

2.H) (1RS,3aSR,4RS,6aRS)-4-(2-Benzo[1,3]dioxol-5-ylmethyl-1-ethyl-3-oxo-decahydro-pyrrolo[3,4-a]pyrrolizin-4-yl)-benzimidamide hydrochloride. Yield 78%. Colourless solid. M.p. 195°–199° C. DEI-MS: 446.3 ([M]$^+$, 22); 201.2 (64); 184.1 (45); 135.1 (100).

EXAMPLE 3

841 mg (12.12 mmol) of hydroxylamine hydrochloride are suspended in 4 ml of DMF and cooled to 0° C. 303 mg (10.1 mmol) of 80% sodium hydride are added slowly. 500 mg (1.13 mmol) of (1RS,3aSR,4RS,6aSR)-4-(5-benzo[1,3]dioxol-5-ylmethyl-4-isopropyl-2,3,3-trimethyl-6-oxo-octahydro-pyrrolo[3,4-c]pyrrol-1-yl)-benzonitrile are dissolved in DMF and added to the reaction mixture. The cooling is thereafter no longer applied. The mixture is stirred at room temperature for 5 days. Thereafter, it is filtered and the solvent is removed in a high vacuum. The mixture is purified by chromatography (RP18, gradient from water to methanol). (1RS,3aSR,4RS,6aSR)-4-(5-Benzo[1,3]dioxol-5-ylmethyl-4-isopropyl-2,3,3-trimethyl-6-oxo-octahydro-pyrrolo[3,4-c]pyrrol-1-yl)-N-hydroxy-benzimidamide is isolated in 66% yield. Colourless solid. ISP-MS: 479.4 ([M+H]$^+$, 100).

EXAMPLE 4

500 mg (1 mmol) of (1RS,3aSR,4RS,6aRS)-4-(2-benzo-[1,3]dioxol-5-ylmethyl-1-isopropyl-3-oxo-decahydro-pyrrolo[3,4-a]pyrrolizin-4-yl)-benzimidamide hydrochloride in a mixture of 10 ml of dichloromethane and 10 ml of a 10% sodium hydrogen carbonate solution are treated with 120 mmol of methyl chloroformate in 2 ml of dichloromethane and stirred vigorously for 30 minutes. Thereafter, the organic phase is separated and the aqueous phase is extracted with dichloromethane. The organic phases are combined, dried with sodium sulphate and evaporated. 360 mg of crude methyl (1RS,3aSR,4RS,6aRS)-amino-{4-(2-benzo[1,3]dioxol-5-ylmethyl-1-isopropyl-3-oxo-decahydro-pyrrolo[3,4-a]pyrrolizin-4-yl)}-phenylmethylene-carbamate are obtained. Yield 70%. ISP-MS: 518.6 ([M+H]+, 100).

REFERENCE EXAMPLE 5

5.A) A mixture of α-amino-isobutyric acid (1.03 g, 10 mmol), 4-bromobenzaldehyde (1.85 g, 10 mmol) and N-piperonyl-maleimide (2.31 g, 10 mmol) in DMF (20 ml) is heated to 90° C. for 16 h. The solvent is distilled off in a vacuum and the residue is separated by chromatography over silica gel (hexane/EtOAc/NEt$_3$ 59.4:39.6:1). Yield 2.17 g (48%) of 2-benzo[1,3]dioxol-5-ylmethyl-4-(4-bromo-phenyl)-6,6-dimethyl-tetrahydro-pyrrolo[3,4-c]pyrrole-1 3-dione.

Colourless platelets. M.p. 149°–150° C. (EtOAc/hexane). FAB-MS: 915.3 (3); 457.1 ([M]$^+$, 67); 225.0 (40); 135.0 (100); 91 (45).

5.B) A mixture of 2-benzo[1,3]dioxol-5-ylmethyl-4-(4-bromo-phenyl)-6,6-dimethyl-tetrahydro-pyrrolo[3,4-c]pyrrole-1,3-dione (2.17 g, 4.75 mmol), 85% formic acid (2.57 g, 47.5 mmol) and 35% formalin solution (0.82 g, 9.5 mmol) is heated to 100° C. for 7 h. After cooling 1N NaOH (40 ml) is added and the mixture is extracted with dichloromethane. The organic phase is dried and concentrated and the residue is separated by chromatography over silica gel (hexane/EtOAc/NEt$_3$ 59.4:39.6:1). Yield 2.06 g (92%) of 2-benzo[1,3]dioxol-5-ylmethyl-4-(4-bromo-phenyl)-5,6,6-trimethyl-tetrahydro-pyrrolo[3,4-c]pyrrole-1,3-dione. Colourless prisms. M.p. 109°–111° C. (MeOH). FAB-MS: 941.0 (1); 471.0 ([M+H]$^+$, 71); 470.0 ([M]$^+$, 21); 469.0 (42); 455.0 (([M—CH$_3$]$^+$, 54); 135.0 (100).

5.C) A solution of 2-benzo[1,3]dioxol-5-ylmethyl-4-(4-bromo-phenyl)-5,6,6-trimethyl-tetrahydro-pyrrolo[3,4-c]pyrrole-1,3-dione (8.49 g, 18.0 mmol) in THF (60 ml) is cooled to −78° C. and a THF solution of lithium triethylborohydride (30.65 mmol) is added. The reaction mixture is stirred at −78° C. for 2 h. and thereafter warmed to 0° C. A saturated NaHCO₃ solution (20 ml) and 30% H₂O₂ (6 ml) are added in succession. The mixture is stirred at 0° C. for a further 1 h. and thereafter the THF is removed by distillation. The aqueous phase is extracted with CH₂Cl₂. The organic phase is dried, the solvent is removed and the residue is separated by chromatography (CH₂Cl₂/CH₃OH 98:2). Yield 5.75 g (67%) 2-benzo[1,3]dioxol-5-ylmethyl-6-(4-bromo-phenyl)-3-hydroxy-5,4,4-trimethyl-tetrahydro-pyrrolo[3,4-c]pyrrol-1-one. Colourless needles. M.p. 158°–159° C. (diethyl ether). FAB-MS: 947.4 (4); 473.2 ([M+H]⁺, 76); 457.2 ([M—CH₃]⁺, 61); 135.0 (100).

5.D) Dry, powdered CaCl₂ (3.91 g, 35.2 mmol) is added to a solution of toluenesulphinic acid (5.49 g, 35.2 mmol) in dry CH₂Cl₂ (60 ml) and the suspension is stirred for 10 min. (argon atmosphere). Thereafter, a solution of 2-benzo[1,3]dioxol-5-ylmethyl-6-(4-bromo-phenyl)-3-hydroxy-5,4,4-trimethyl-tetrahydro-pyrrolo[3,4-c]pyrrol-1-one (5.55 g, 11.7 mmol) in CH₂Cl₂ (20 ml) is added. The mixture is stirred for 19 h. Subsequently, saturated NaHCO₃ solution (20 ml) is added and the mixture is extracted with CH₂Cl₂. The organic phase is washed with H₂O and dried (Na₂SO₄). The solvent is removed in a vacuum and the residue is purified by chromatography (hexane/EtOAc/ NEt₃ 74:25:1). Yield 5.29 g (74%) of 2-benzo[1,3]dioxol-5-ylmethyl-4-(4-bromo-phenyl)-5,6,6-trimethyl-3-oxo-octahydro-pyrrolo[3,4-c]pyrrol-1-yl toluene sulphonate. Colourless prisms. M.p. 172°–173° C. (EtOAc/hexane). FAB-MS: 1223.3 (1); 1067.2 (1); 611.0 ([M+H]⁺, 30); 455.1 (62); 135.0 (100).

REFERENCE EXAMPLE 6

In analogy to Example 5, from proline, bromobenzaldehyde and N-piperonyl-maleimide there is obtained:

6.A) In analogy to Example 5.A): 2-benzo[1,3]dioxol-5-ylmethyl-4-(4-bromo-phenyl)-hexahydro-pyrrolo[3,4-a]pyrrolizine-1,3-dione. Yield 20%. Colourless crystals. M.p. 134°–136° C. (MeOH). FAB-MS: 938.8 (4); 469.1 ([M]⁺, 100); 237.0 (38); 135.1 (91).

6.B) A solution of 2-benzo[1,3]dioxol-5-ylmethyl-4-(4-bromo-phenyl)-hexahydro-pyrrolo[3,4-a]pyrrolizine-1,3-dione (2.18 g, 4.63 mmol) in THF (20 ml) is cooled to −78° C. and a THF solution of lithium triethylborohydride (7.87 mmol) is added. The reaction mixture is stirred at −78° C. for 0.5 h. and thereafter warmed to 0° C. A saturated NaHCO₃ solution (5 ml) and 30% H₂O₂ (1.5 ml) are added in succession. The mixture is stirred at 0° C. for a further 1 h. and thereafter the THF is removed by distillation. The aqueous phase is extracted with CH₂Cl₂. The organic phase is dried and the solvent is removed. Toluenesulphinic acid (2.17 g, 13.9 mmol), CaCl2 (1.54 g, 13.9 mmol) and CH₂Cl₂ (40 ml) are added to the resulting crude hydroxylactam and the mixture is stirred under an argon atmosphere for 24 h. A saturated NaHCO₃ solution is added and the mixture is extracted with CH₂Cl₂. The organic phase is washed with NaHCO₃ solution, dried with Na₂SO₄, the solvent is removed and the residue is separated by chromatography (hexane/EtOAc/NEt₃ 74:25:1). Yield 2.06 g (73%) of 2-benzo[1,3]dioxol-5-ylmethyl-4-(4-bromo-phenyl)-3-oxo-decahydro-pyrrolo[3,4-a]pyrrolizin-1-yl toluenesulphonate. Colourless prisms. M.p. 199°–201° C (EtOAc). FAB-MS: 1218.8 (4); 609.0 ([M+H]⁺, 100); 453.0 (81); 307.1 (33); 135.0 (86).

REFERENCE EXAMPLE 7

Nitrile starting material for Example 1

7.A) Methylmagnesium chloride (6.54 mmol, as a solution in THF) is added to a solution of ZnCl₂ (3.92 mmol, as a 0.5M solution in THF) in dry CH₂Cl₂ (30 ml) and the mixture is stirred for 30 min. (argon atmosphere). Subsequently, a solution of 2-benzo[1,3]-dioxol-5-ylmethyl-4-(4-bromo-phenyl)-5,6,6-trimethyl-3-oxo-octahydro-pyrrolo[3,4-c]pyrrol-1-yl toluenesulphonate (2 g, 3.27 mmol) in CH₂Cl₂ is added and the reaction mixture is stirred for 13 h. Thereafter, 1M HCl solution is added and the mixture is neutralized with NaHCO₃ solution and extracted with CH₂Cl₂. The organic phase is dried, the solvent is removed in a vacuum and the residue is purified by chromatography (hexane/EtOAc/NEt₃ 49.5:49.5:1). Yield 1.15 g (75%) of 2-benzo[1,3]dioxol-5-ylmethyl-6-(4-bromo-phenyl)-3,4,4,5-tetramethyl-hexahydro-pyrrolo[3,4-c]pyrrol-1-one.

Colourless solid. M.p. 142°–144° C. (toluene). FAB-MS: 943.3 (6); 471.3 ([M+H]⁺, 82); 455.2 ([M—CH₃]⁺, 45); 135.0 (100).

7.B) A suspension of 2-benzo[1,3]dioxol-5-ylmethyl-6-(4-bromo-phenyl)-3,4,4,5-tetramethyl-hexahydro-pyrrolo[3,4-c]pyrrole-1-one (1.00 g, 2.12 mmol) and copper(1) cyanide (0.76 g, 8.48 mmol) in DMF (30 ml) is heated under reflux for 17 h. (argon atmosphere). Thereafter, part of the DMF (about 20 ml) is removed by distillation and then dichloromethane (30 ml) and concentrated aqueous ammonia solution (10 ml) are added. The mixture is stirred vigorously for one hour. The blue aqueous phase is separated and the organic phase is washed twice with ammonia solution and once with water. The solvent is removed and the residue is purified by chromatography (hexane/EtOAc/ NEt₃ 49.5:49.5:1). Yield: 0.55 g (62%) (1RS,3aSR,4SR,6aSR)-4-(5-benzo[1,3]dioxol-5-ylmethyl-2,3,3,4-tetramethyl-6-oxo-octahydro-pyrrolo[3,4-c]pyrrole-1-yl)-benzonitrile. Colourless crystals. M.p. 165°–166° C. (EtOAc/diethyl ether). FAB-MS: 835.3 (20); 418.2 ([M+H]⁺, 100); 403.1 (52); 135.0 (40).

REFERENCE EXAMPLE 8

Nitrile starting materials for Examples 2.A) to G) and 3.

1. In analogy to Example 7, from 2-benzo[1,3]dioxol-5-ylmethyl-4-(4-bromo-phenyl)-5,6,6-trimethyl-3-oxo-octahydro-pyrrolo[3,4-c]pyrrol-1-yl-toluenesulphonate 8.A.a) with ethylmagnesium chloride, via 2-benzo[1,3]-dioxol-30 5-ylmethyl-6-(4-bromo-phenyl)-3-ethyl-4,4,5-trimethyl-hexahydro-pyrrolo[3,4-c]pyrrol-1-one, yield 76%, colourless needles, m.p. 156°–157°0 C. (CHCl₃/hexane), FAB-MS: 971.3 (5); 485.1 ([M+H]⁺, 68); 135.0 (100), there is obtained 8.A.b) (1RS,3aSR,4SR,6aSR)-4-(5-benzo[1,3]dioxol-5-ylmethyl-4-ethyl-2,3,3-trimethyl-6-oxo-octahydro-pyrrolo[3,4-c]pyrrol-1-yl)-benzonitrile. Yield 40%. Colourless needles. M.p. 188°–190° C. (EtOAc). FAB-MS: 863.3 (9); 432.2 ([M+H]⁺, 100); 416.2 (72); 135.0 (99), 8.B.a) with isopropylmagnesium chloride via 2-benzo[1,3]-dioxol-5-ylmethyl-6-(4-bromo-phenyl)-3-isopropyl-4,4,5-trimethyl-hexahydro-pyrrolo[3,4-c]pyrrol-1-one, yield 35%, colourless needles, m.p. 146°–147° C. (CHCl₃/hexane), FAB-MS: 999.2 (2); 499.2 ([M+H]⁺, 78); 135.1 (100), there is obtained 8.B.b) (1RS,3aSR,4SR,6aSR)-4-(5-benzo[1,3]dioxol-5-ylmethyl-4-isopropyl-2,3,3-trimethyl-6-oxo-octahydro-pyrrolo[3,4-c]pyrrol-1-yl)-benzonitrile. Yield: 55%. Colourless prisms. M.p. 160°–162° C. (EtOAc). FAB-MS: 891.4 (13); 446.2 ([M+H]⁺, 100); 430.2 (63); 135.0 (63), 8.C.a) with cyclohexylmagnesium chloride, via 2-benzo[1,3]-dioxol-5-ylmethyl-6-(4-bromo-phenyl)-3-cyclohexyl- 4,4,5-trimethyl-hexahydro-pyrrolo[3,4-c]pyrrol-1-one, yield 31%, colourless crystals. m.p. 148°–149° C. (CHCl₃/hexane), FAB-MS: 1079.9 (4); 539.4 ([M+H]⁺, 100); 523.4 (61); 135.0 (41), there is obtained 8.C.b) (1RS,3aSR,4SR,6aSR)-4-(5-benzo[1,3]dioxol-5-ylmethyl-4-cyclohexyl-2,3,3-trimethyl-6-oxo-octahydro-pyrrolo[3,4-c]pyrrol-1-yl)-benzonitrile. Yield: 62%. Colourless needles. M.p. 114°–160° C. (CHCl₃/hexane). FAB-MS: 971.4 (6); 486.2 ([M+H]⁺, 93); 484.2 (40); 135.0 (100).

2. In analogy to Example 7, from 2-benzo[1,3]dioxol-5-ylmethyl-4-(4-bromo-phenyl)-3-oxo-decahydro-pyrrolo[3,4-c]pyrrolizin-1-yl toluenesulphonate 8.D.a) with isopropylmagnesium chloride, via 2-benzo[1,3]-dioxol-5-ylmethyl-4-(4-bromo-phenyl)-1-isopropyl-octahydro-pyrrolo[3,4-a]pyrrolizin-3-one, yield 52%, yellowish oil, FAB-MS: 995.1 (3); 497.1 ([M+H]⁺, 100); 307.0 (78), there is obtained 8.D.b) 4-(2-benzo[1,3]dioxol-5-ylmethyl-1-isopropyl-3-oxo-decahydro-pyrrolo[3,4-a]pyrrolizin-4-yl)-benzonitrile. Yield: 56%. Colourless needles. M.p. 152–153 (EtOH). FAB-MS: 887.7 (4); 444.3 ([M+H]⁺, 100); 307.1 (20); 184.1 (36); 135.0 (64), 8.E.a) with cyclohexylmagnesium chloride, via 2-benzo[1,3]-dioxol-5-ylmethyl-4-(4-bromophenyl)-1-cyclohexyl-octahydro-pyrrolo[3,4-a]pyrrolizin-3-one, yield 21%, colourless needles, m.p. 143°–146° C. (CHCl₃/hexane), FAB-MS: 1074.9 (9); 536.9 ([M+H]⁺, 100); 135.0 (32), there is obtained 8.E.b) 4-(2-benzo[1,3]dioxol-5-ylmethyl-1-cyclohexyl-3-oxo-decahydro-pyrrolo[3,4-a]pyrrolizin-4-yl)-benzonitrile. Yield: 66%. Colourless needles. M.p. 204°–207° C. (EtOAc/hexane). FAB-MS: 967.3 (2); 484.2 ([M+H]⁺, 100); 307.0 (19); 154.1 (80); 135.0, 8.F.a) with phenylmagnesium chloride, via 2-benzo[1,3]dioxol-5-ylmethyl-4-(4-bromo-phenyl)-1-phenyl-octahydro-pyrrolo[3,4-a]pyrrolizin-3-one, yield 90%, colourless needles, m.p. 158°–160° C. (hexane/EtOAc), FAB-MS: 531.1 ([M+H]⁺, 100); 237.0 (31); 135.0 (78), there is obtained 8.F.b) 4-(2-benzo[1,3]dioxol-5-ylmethyl-3-oxo-1-phenyl-decahydro-pyrrolo[3,4-a]pyrrolizin-4-yl)-benzonitrile. Yield 61%. Colourless prisms. M.p. 154°–156° C. (EtOAc). FAB-MS: 955.3 (7); 478.1 ([M+H]⁺, 100); 184.1 (31); 135.0 (61), 8.G.a) with cyclopropylmagnesium chloride, via 2-benzo-[1,3]dioxol-5-ylmethyl-4-(4-bromo-phenyl)-1-cyclopropyl-octahydro-pyrrolo[3,4-a]pyrrolizin-3-one, yield 48%, yellowish oil, FAB-MS: 991.3 (16); 495.2 ([M+H]⁺, 100), there is obtained 8.G.b) 4-(2-benzo[1,3]dioxol-5-ylmethyl-1-cyclopropyl-3-oxo-decahydro-pyrrolo[3,4-a]pyrrolizin-4-yl)-benzonitrile. Yield 71%. Colourless prisms. M.p. 120°–122° C. (EtOAc). FAB-MS: 883.4 (4); 442.2 ([M+H]⁺, 100); 307.1 (31); 184.1 (40).

REFERENCE EXAMPLE 9

Nitrile starting material for Example 2H

Ethylmagnesium chloride (9.86 mmol, as a solution in THF) is added to a solution of ZnCl₂ (5.92 mmol, as a solution in diethyl ether) in dry CH₂Cl₂ (15 ml) and the mixture is stirred for 30 min. (argon atmosphere). Subsequently, a solution of 2-benzo[1,3]dioxol-5-ylmethyl-4-(4-bromo-phenyl)-3-oxo-decahydro-pyrrolo[3,4-c]pyrrolizin-1-yl toluene sulphonate (3.0 g, 4.93 mmol) in CH₂Cl₂ (15 ml) is added and the reaction mixture is stirred for 16 h. Thereafter, 1M HCl is added and the mixture is subsequently neutralized and extracted with CH₂Cl₂. The organic phase is dried, the solvent is removed in a vacuum and the residue is purified by chromatography (hexane/EtOAc/NEt₃ 66:33:1). Yield: 1.69 g (71%) of a yellowish oil consisting of a mixture of two isomers. This substance is treated with CuCN (1.25 g, 14 mmol) and de-gassed DMF (35 ml) and the mixture is heated under reflux for 28 h. (argon atmosphere). Thereafter, part of the DMF (about 20 ml) is removed by distillation and subsequently dichloromethane (30 ml) and concentrated aqueous ammonia solution (10 ml) are added. The mixture is stirred vigorously for one hour. The blue aqueous phase is separated and the organic phase is washed twice with ammonia solution and once with water. The solvent is removed and the residue is purified by chromatography (hexane/EtOAc/NEt₃ 49.5:49.5:1). Yield 0.805 g of 4-(2-benzo[1,3]dioxol-5-ylmethyl-1-30 ethyl-3-oxo-decahydro-pyrrolo[3,4-a]pyrrolizin-4-yl)-benzonitrile. Colourless prisms. M.p. 150°–151° C. (EtOAc). FAB-MS: 859.5 (14); 430.3 ([M+H]⁺, 100); 135.1 (18).

A compound of formula I, a solvate or salt thereof can be used in a manner known per se as the active ingredient for the production of pharmaceutical preparations, e.g. of tablets and capsules of the following composition:

Example A

| | Per Tablet |
|---|---|
| Active ingredient | 200 mg |
| Microcrystalline cellulose | 155 mg |
| Corn starch | 25 mg |
| Talc | 25 mg |
| Hydroxypropylmethylcellulose | 20 mg |
| | 425 mg |

Example B

| | Per capsule |
|---|---|
| Active ingredient | 100.0 mg |
| Corn starch | 20.0 mg |
| Lactose | 95.0 mg |
| Talc | 4.5 mg |
| Magnesium stearate | 0.5 mg |
| | 220.0 mg |

We claim:

1. A compound of the formula:

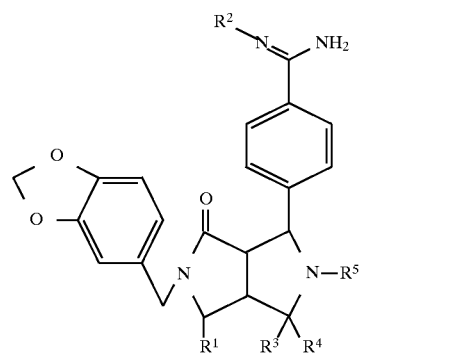

wherein:

$R^1$ is lower-alkyl, cycloalkyl or phenyl;

$R^2$ is H, OH or C(O)O—A, wherein A is lower-alkyl, cycloalkyl or phenyl; and $R^3$ is H and $R^4$ and $R^5$ taken together are trimethylene; or a hydrate, solvate or a physiologically usable salt thereof.

2. The compound of claim 1 wherein $R^3$ is hydrogen and $R^4$ and $R^5$ taken together are trimethylene whereby said compound is of the formula:

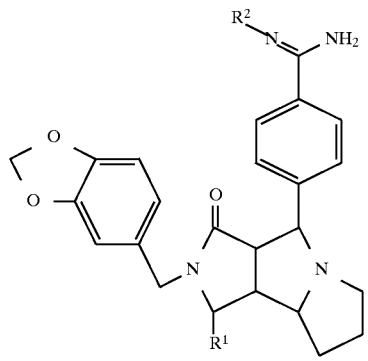

wherein $R^1$ and $R^2$ are as in claim 1.

3. The compound of claim 2 wherein $R^1$ is lower-alkyl.

4. The compound of claim 3 wherein $R^2$ is hydrogen.

5. The compound of claim 4 wherein said compound is (1RS,3aSR,4RS,6aRS)-4-(2-benzo[1,3]dioxol-5-ylmethyl-1-isopropyl-3-oxo-decahydro-pyrrolo[3,4-a]pyrrolizin-4-yl)- benzimidamide.

6. The compound of claim 4 wherein said compound is (1RS,3aSR,4RS,6aRS)-4-(2-benzo[1,3]dioxol-5-ylmethyl-1-ethyl-3-oxo-decahydro-pyrrol[3,4-a]pyrrolizin-4-yl)-benzimidamide.

7. The compound of claim 3 wherein $R^2$ is C(O)O—A.

8. The compound of claim 7 wherein A is lower-alkyl.

9. The compound of claim 8 wherein said compound is methyl (1RS,3aSR,4RS,6aRS)-amino-{4-(2-benzo[1,3]dioxol-5-ylmethyl-1-isopropyl-3-oxo-decahydro-pyrrolo[3,4-a]pyrrolizin-4-yl)}-phenylmethylene-carbamate.

10. The compound of claim 2 wherein $R^1$ is cycloalkyl.

11. The compound of claim 10 wherein $R^2$ is hydrogen.

12. The compound of claim 11 wherein said compound is (1RS,3aSR,4RS,6aRS)-4-(2-benzo[1,3]dioxol-5-ylmethyl-1-cyclopropyl-3-oxo-decahydro-pyrrolo[3,4-a]pyrrolizin-4-yl)-benzimidamide.

13. The compound of claim 11 wherein said compound is (1RS,3aSR,4RS,6aRS)-4-(2-Benzo[1,3]dioxol-5-ylmethyl-1-cyclohexyl-3-oxo-decahydro-pyrrolo[3,4-a]pyrrolizin-4-yl)-benzimidamide.

14. The compound of claim 2 wherein $R^1$ is phenyl.

15. The compound of claim 14 wherein $R^2$ is hydrogen and said compound is (1RS,3aSR,4RS,6aRS)-4-(2-Benzo[1,3]dioxol-5-ylmethyl-3-oxo-1-phenyl-decahydro-pyrrolo[3,4-a]pyrrolizin-4-yl)-benzimidamide.

16. A method of treating thrombosis in a host in need of such treatment, which method comprises administering to said host a pharmaceutical composition, in a phamaceutically acceptable carrier, a compound of the formula:

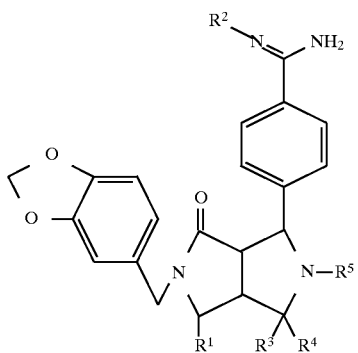

wherein:

$R^1$ is lower-alkyl, cycloalkyl or phenyl;

$R^2$ is H, OH or C(O)O—A, wherein A is lower-alkyl, cycloalkyl or phenyl; and $R^3$ is H and $R^4$ and $R^5$ taken together are trimethylene;

or a hydrate, solvate or a physiologically usable salt thereof; in an effective amount sufficient to treat said thrombosis.

17. The method of claim 16 wherein said compound is administered in an amount from about 0.1 to 20 mg/kg per day.

18. The method of claim 17 wherein $R^3$ is hydrogen and $R^4$ and $R^5$ taken together are trimethylene.

19. The method of claim 18 wherein $R^1$ is lower-alkyl.

20. The method of claim 19 wherein $R^2$ is hydrogen.

21. The method of claim 20 wherein said compound is (1RS,3aSR,4RS,6aRS)-4-(2-benzo[1,3]dioxol-5-ylmethyl-1-ethyl-3-oxo-decahydro-pyrrolo[3,4-a]pyrrolizin-4-yl)-benzimidamide.

22. The method of claim 21 wherein said compound is administered in an amount from about 0.5 to 4 mg/kg per day.

23. The method of claim 20 wherein said compound is (1RS,3aSR,4RS,6aRS)-4-(2-benzo[1,3]dioxol-5-ylmethyl-1-isopropyl-3-oxo-decahydro-pyrrolo[3,4-a]pyrrolizin-4-yl)-benzimidamide.

24. The method of claim 23 wherein said compound is administered in an amount from about 0.5 to 4 mg/kg per day.

25. The method of claim 18 wherein $R^1$ is cycloalkyl.

26. The method of claim 25 wherein $R^2$ is hydrogen.

27. The method of claim 26 wherein said compound is (1RS,3aSR,4RS,6aRS)-4-(2-benzo[1,3]dioxol-5-ylmethyl-1-cyclopropyl-3-oxo-decahydro-pyrrolo[3,4-a]pyrrolizin-4-yl)-benzimidamide.

28. The method of claim 27 wherein said compound is administered in an amount from about 0.5 to 4 mg/kg per day.

* * * * *